United States Patent

Seymour

[11] 4,042,328
[45] Aug. 16, 1977

[54] ON-LINE ANALYZER

[76] Inventor: George W. Seymour, 2841 Parkwood Drive, Brunswick, Ga. 31520

[21] Appl. No.: 674,261

[22] Filed: Apr. 6, 1976

[51] Int. Cl.$^2$ .................. D21C 7/12; G01N 25/48
[52] U.S. Cl. .................. 23/230 R; 23/230 A; 73/190 R; 162/49
[58] Field of Search ............ 23/230 R, 230 A; 73/190 R; 162/49, 238

[56] References Cited

U.S. PATENT DOCUMENTS

| | | | |
|---|---|---|---|
| 1,594,264 | 7/1926 | Howard | 23/230 A |
| 3,471,582 | 10/1969 | Lupfer | 23/230 A X |
| 3,578,405 | 5/1971 | Woodle | 23/230 R |
| 3,768,973 | 10/1973 | Wasilewski | 23/230 R |
| 3,856,467 | 12/1974 | Picker | 23/230 R |
| 3,888,726 | 6/1975 | Hultman | 162/49 |

Primary Examiner—Joseph Scovronek
Attorney, Agent, or Firm—Jones, Tullar & Cooper

[57] ABSTRACT

This invention relates to a continuous method for determining the concentration of a chemical component in a fluid stream, using the heat of reaction or enthalpy as a measure of the concentration, when the chemical component whose concentration is to be determined is reacted with an appropriate reagent. The improvement of the present invention resides in the regulation of the temperature of the reagent stream to approximate the temperature of the reacted mixture product stream. An additional embodiment of the present invention shows the regulation of the temperature of the sample stream such that the final reacted mixture temperature will substantially equal or closely approximate the temperature of the reagent stream.

7 Claims, 3 Drawing Figures

ON-LINE ANALYZER

SUMMARY OF THE INVENTION

The present invention relates to a process for determining the concentration of chemicals either along, or in combination with other materials which may ordinarily cause difficulty in determining concentration by other means. This process uses specific reagents, combined with means to determine the flow rates of both the samples containing the chemical of which the concentration is to be determined, and the reagents; and means to determine the temperature change upon the reaction of the chemical being measured in the sample with the specific reagent or reagents.

One of the most important features of the present invention is that the regulation of the temperature of the reagent stream or the sample stream to approximate the temperature of the reacted mixture product stream allows for the elimination or reduction of the effects of volume measurements from the calculations in the determination of concentration.

One advantage of the present invention precludes the necessity of adjusting the reagent flow in response to a varying concentration of the chemical in the sample stream to be measured, since the reagent is applied in excess. However, this does not preclude the adjustment of flows of either the sample or reagent streams by suitable means such as computers, instruments or operators, in order to gain sensitivity, reduce chemical usages, or to otherwise improve the analysis.

A further advantage of the present invention is that the process is not limited to liquid solutions but can be used in any combination of liquid, solid suspensions, or gas reactions as long as the change in temperature due to the reaction is related to the chemical concentrations in the sample stream.

Another advantage is that the flow rates of the sample and reagent streams may be measured by any known flow measuring means and the temperatures of these streams may be mesured by any method of sufficient accuracy.

Still another advantage of the present invention is that it may be used to determine the composition of the sample by the use of any reagent or mixture of reagents reacting with the component being measured to cause a $\Delta T$. This reaction can be oxidation-reduction, acid-base, ion exchange, heat of dilution, precipitation, change of phase, or any combination of these reactions or other art recognized reactions as long as an exothermic or endothermic reaction is produced.

The process of the present invention is for determining the concentration of at least one chemical substance in a moving fluid sample stream. The fluid sample stream may contain many chemical compounds. The reagent is selected on the basis of the overall chemical concentration determinations desirable. If it is desired that only the concentration of one component or chemical substance is to be measured, a reagent is chosen which will react solely with that chemical substance. However, the total alkalinity or reducing capacity of a sample stream may be determined through the selection of a reagent which will react with all of the chemical substances in the sample stream which possess the desired chemical properties to be determined. Therefore, a single reagent may react with a number of different chemical substances in a sample stream in order to determine an overall chemical property.

Obviously, if desired, a mixture of reagents may be utilized to determine either a single component or a mixture of components. Where a mixture of reagents are employed, the determination described therein can be adjusted in an obvious manner to take into account the use of such a mixture.

A better understanding of the invention will be derived from the following description considered in connection with the accompanying drawings. It is expressly understood, however, that the drawings are from the purpose of illustration and description only and are not intended as a definition of the limitations of the invention.

Figure 1:
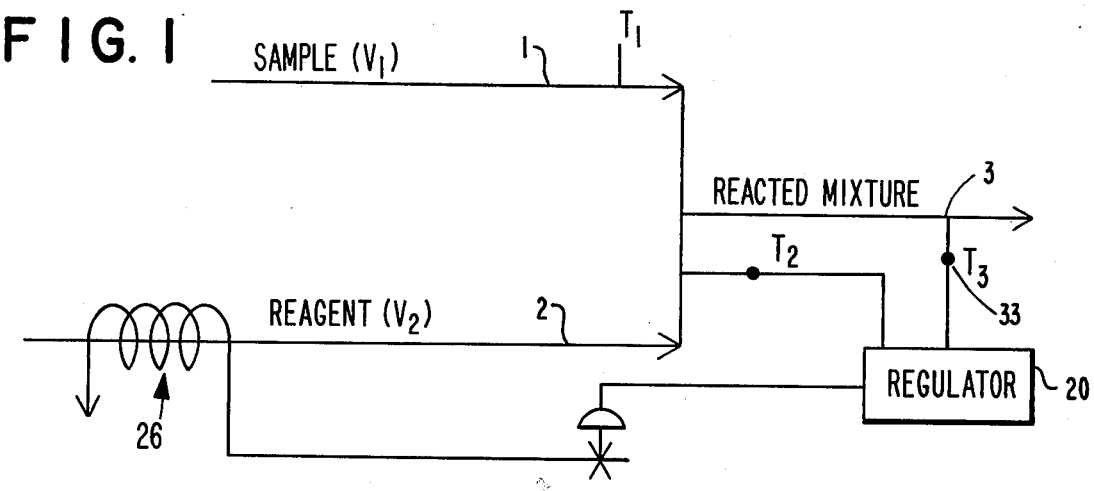
FIG. 1 is a diagrammatic representation of the flow calorimeter embodying the underlying principle of the present invention.

With respect to FIG. 1, sample stream 1 represents the stream containing the chemical component whose concentration is to be measured. Reagent stream 2 represents the reagent to be added to sample stream 1 which will react with the active chemical of the sample stream 1 upon mixing in stream 3. The reacting substances will either produce heat or absorb heat in the reaction. The temperature of the reaction stream 3 is measured by temperature sensor 33 which may either be a thermocouple or any other temperature sensing system of the required reliability, accuracy and range. This temperature is transferred into a temperature regulator 20 which controls the reagent stream temperature using a heating or cooling element 26. The temperature regulator 20 adjusts the temperature of the reagent stream 2 to approximate the temperature of the reacted mixture stream 3.

The result of either an exothermic or endothermic reaction may be used to determine the concentration of the active chemical in the sample steam through the use of the following formula:

Equation 1

$$X = \frac{T_3V_1 + T_3V_2 - T_1V_1 - T_2V_2}{CV_1}$$

or rewritten $$X = \frac{V_1(T_3 - T_1) + V_2(T_3 - T_2)}{CV_1}$$

where
$T_1$, $T_2$, $T_3$ represent the temperature of corresponding streams 1, 2, 3 in FIG. 1 measured in degrees Centigrade,
$V_1$ represents the flow rate of the sample stream,
$V_2$ represents the flow rate of the reagent stream,
C is a factor correcting for heat capacity, heat of reaction, degree of completion of the reaction and conversion to the desired engineering units, $$C = \frac{(\Delta H_{reaction}) \text{ (heat capacity of the sample stream)}}{\text{molecular weight of the chemical substance being determined}} \times \% \text{ completion}$$

X is the concentration of the active chemical in the sample stream.

Whenever the temperature, $T_2$, of the reagent stream 2, equals the temperature, $T_3$, of the reacting stream 3, the above equation is reduced to:

$$X = \frac{(T_3 - T_1)}{C} \qquad \text{Equation 2}$$

Therefore, the effect of the temperature regulator 26 in equating $T_3$ and $T_2$ completely eliminates the effects of the flow rates from the calculations.

It is obvious from the preceding equations that the present invention would give it the maximum benefits in accuracy when the reagent stream was conditioned to exactly the same temperature as the final reacted mixture temperature. In many cases this total conditioning may not be either practical or possible. Increasing or decreasing the temperature of the reagent stream as close as possible to the temperature of the reacted mixture stream temperature will proportionately increase the accuracy of the active chemical concentration determination.

Alternative methods of approaching the accomplishment of the desired relationship of equalizing the temperature of the reagent stream 2 and the reacted mixture stream 3 are considered a part of the present invention. For example, the reacted mixture stream may be used in a heat exchange with the reagent stream to increase or decrease the temperature of the reagent stream toward the temperature of the reacted mixture stream as demonstrated in FIG. 2. Volume measurements must be recorded for both the reagent and sample streams as the temperature differential between $T_3$ and $T_2$ may not be small enough to be negligible when the concentration of the sample stream is determined by equation 1. However, as $T_2$ approaches $T_3$, volume measurements have less effect on the determination of the concentration of the chemical in the sample stream and thus minimize errors from volumetric flow volumetric flow determinations. Regulation of the temperature of the reagent stream to equal or approach the temperature of the reacted mixture product stream not only eliminates or reduces volumetric determination errors but also the temperature difference between the sample stream and reacted mixture product stream temperature is at a maximum thus reducing temperature measurement errors.

The temperature of the sample stream, instead of the reagent stream, may be regulated by any of the means contemplated such that the final reacted mixture temperature will approximate the temperature of the reagent stream. This has the same effect as the direct regulation of the reagent stream itself in the elimination of volume errors and reduction in the temperature measurement errors. In some cases this regulation of the temperature of the sample stream may be the most practical method to accomplish the increased accuracy as in this invention.

Any of the systems described above or shown in FIGS. 1 and 2 can be used to determine the effective alkali content of the kraft white liquor in the kraft pulping process. The major constitutents of this liquor are sodium sulfide, sodium hydroxide, sodium carbonate with smaller amounts of other chemicals. The ragent used in the analysis is sodium bicarbonate so that the reacted product will be primarily sodium carbonate. This performs several advantageous functions. The sodium bicarbonate will react with only the hydroxide and sulfide ions forming carbonate and bisulfide ions. The heat produced will represent the desired available alkali for the cooking reaction for which the white liquor is used. The end product is recoverable and is simply put back into the green liquor since the composition is the same as the green liquor. The product is also non-corrosive and highly alkaline as compared to using an acid as the reagent.

Figure 2:
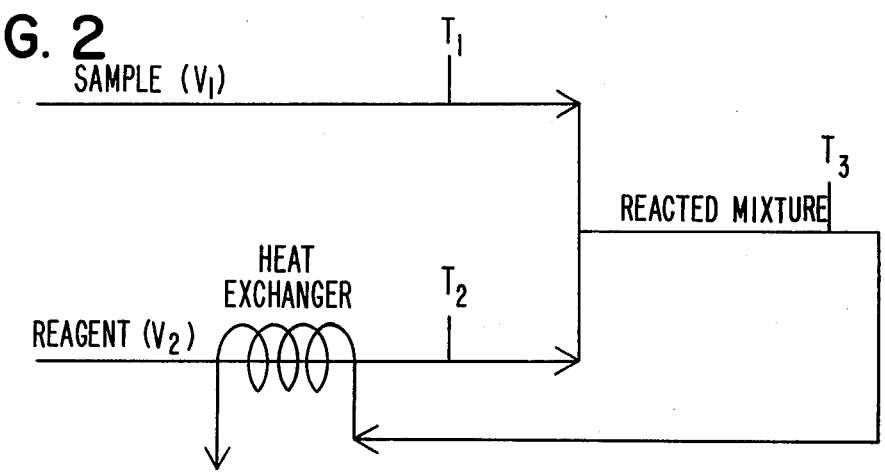
FIG. 2 is a schematic diagram of a flow calorimeter where the temperature of the reagent stream is raised or lowered toward the temperature of the final mixed and reacted fluid by using the reacted mixed stream in a heat exchanger with the reagent stream.

The kraft black liquor that is produced in the cooking process using the above mentioned white liquor on wood chips contains an excess of alkali in addition to the sodium lignates produced in the reaction. The analytical systems as shown in FIGS. 1 and 2 can be used to determine the residual effective alkali in this black liquor. This residual effective alkali is an important function for the process of the cooking reaction, for the efficient use of white liquor, and for the proper operation of the washing and evaporation operations. The reagent in this concentration determination can also be sodium bicarbonate as in the white liquor analysis. The sodium bicarbonate will react only with the effective alkali remaining in the materials in the liquor. The following equation may represent the reaction:

Equation 3
$$NaHCO_3 + NaOH \rightarrow Na_2CO_3 + H_2O \quad \Delta H_R = -9,157 \text{ cal/mol}$$

The concentration of the sodium hydroxide may be determined through the use of either Equation 1 or Equation 2 with the respective process as shown in FIG. 2 or FIG. 1. The temperature of the reagent stream, the sample stream and the reacted mix stream are recorded and if the temperature of the reagent stream equals or closely approximates the temperature of the reacted mix stream, volumetric measurements need not be taken as Equation 2 will be used. The amount of sodium hydroxide in the sample stream will equal the temperature differential measured between the reacted mix stream and the sample stream divided by the reaction factor C. The reaction factor C equals the heat of reaction of Equation 3 times the heat capacity of sodium hydroxide solution divided by the molecular weight of sodium hydroxide:

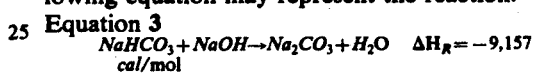

Equation 4

When the temperature differential is divided by the reaction factor, the amount of sodium hydroxide present in the volumetric flow rate of the sample stream is determined.

If however, the reagent stream temperature does not closely approximate the reacted mixture stream temperature such as in a system as demonstrated in FIG. 2, volumetric flow measurements of the sample stream and the reagent stream must be made and the active chemical concentration of the sample stream must be determined through the use of Equation 1. The volumetric measurements of the sample stream plus the reagent stream equal the volumentric flow of the reacted mixture stream.

In the above examples where sodium bicarbonate was to be used as the reagent, it is understood that any chemical with similar properties of pH and reactivity could be used for these reactions. The main objective of the reagent in these cases is to react with the samples such that the pH of the resultant reacted mixture will be lowered by at least two pH units below the sample pH. This will assure that the reaction is approximately 99% complete. This degree of completeness can be determined by additional sensors in the system.

Any additional sensors that are placed in the system to determine the degree of completeness of the reaction, can also be used to correct the calculation of the sample concentration or to take corrective actions in the control of the reaction. Another example of an additional sensor that might be useful in some applications is a temperature probe placed far downstream to determine if any additional reaction has taken place after the initial temperature determination of the reacted mix stream. Any additional sensors placed in the system for this purpose would not constitute an improvement over the system herein described.

Figure 3:
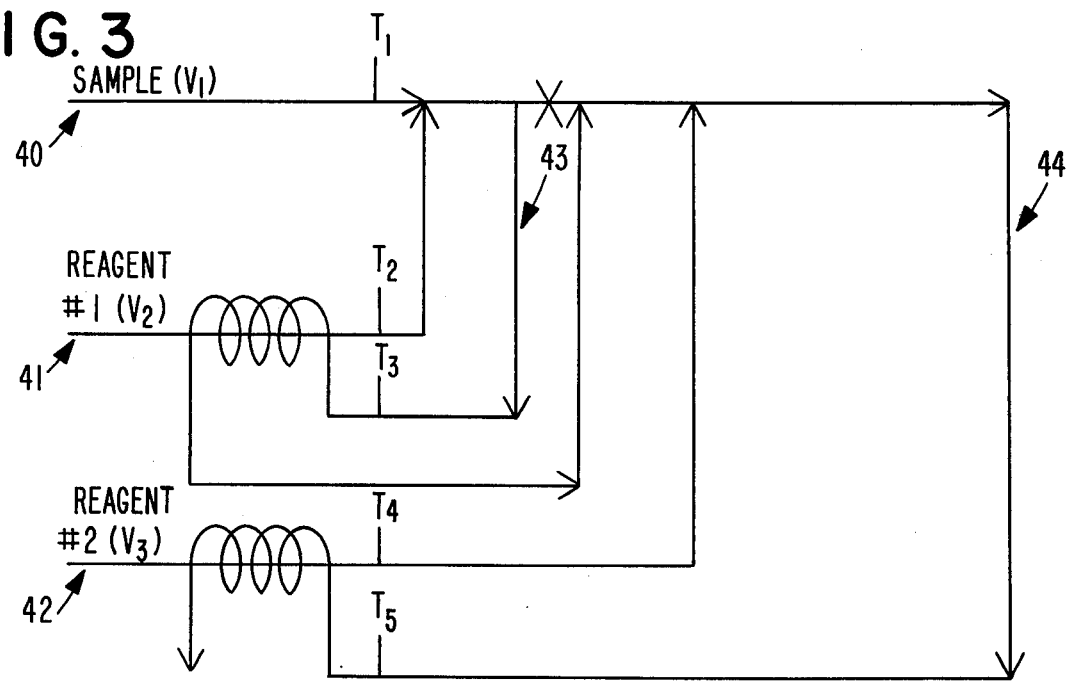
FIG. 3 is a diagrammatic representation of a flow calorimeter in which a plurality of reagents may be used.

FIG. 3 demonstrates a concentration determining scheme where more than one reagent is used in multiple or sequential analysis. Upon the addition of reagent stream 41 or 42 to the sample stream 40, the subsequent reacted mixture streams 43 and 44 are recycled in heat exchange with the respective reagent streams, thus regulating the temperature of the reagent streams to approximate the temperature of the reacted mixture streams.

In the use of multiple reagent streams, external heat or cooling sources may also be used to equate the temperature or the reagent stream with the temperature of the reacted mixture stream which is formed upon the reaction of the active chemical in the moving fluid sample stream with the corresponding reagent stream to be temperature regulated.

When a plurality of reagent streams are used, concentrations of active chemicals are determined and continuously measured immediately after the addition of a reagent stream but before the addition of the following sequential reagent stream through the use of temperature measurements and volumetric flow measurements if necessary. Through this means only may the effect of the individual reagent stream on the sample stream be determined. Once the initial reagent stream has mixed with the sample stream, the resultant reacted mixture stream becomes the sample stream for temperature and volumetric flow measurements in Equations 1 and 2 when determining the effect of the next sequential reagent stream.

This process may be used for the differential analysis of sodium sulfide and sodium thiosulfate in the green liquor produced in a kraft recovery furnace. This differential analysis requires sodium bicarbonate as the first reagent 41 to determine the alkalinity and therefore the sodium sulfide content of the liquor and a second reagent 42 such as hydrogen peroxide for the determination of the total reducing capacity. The difference between these two values is the sodium thiosulfate content. This determination is important in the efficient operation of the recovery operation in pulp mills. Control of the thiosulfate content in the cooking liquor is also important in reducing the corrosivity of the cooking liquor.

The dual analysis may be used in determining the sulfur dioxide concentrations in sulfite cooking liquor. Sulfite cooking liquor is generally composed of sulfur dioxide dissolved in a water solution containing a base such as sodium, ammonia, calcium, magnesium or some other alkaline material. Chemically, this solution is considered to be a mixture of sulfurous acid and sodium sulfite if sodium is the base present. The total concentration of sulfur dioxide in both the free and the combined states may be determined through the addition of a reagent which will measure the total reducing capacity such as hydrogen peroxide. The amount of free sulfur dioxide is determined by the measurement of acidity through the addition of a basic reagent such as sodium hydroxide. The concentration of combined sulfur dioxide, that is the amount of sulfur dioxide which has combined with a base, may be calculated by subtracting the concentration of free sulfur dioxide present in sulfurous acid from the total concentration of sulfur dioxide present in the sample stream.

A further example of the use of a dual analysis as demonstrated in FIG. 3 is the analysis of an alkaline oxidizing solution. This particular example is for sodium hypochlorite but would apply equally well for an alkaline peroxide solution. One of several reagent combinations that will suffice for this analysis of the alkaline hypochlorite solutions is sodium bicarbonate for determination of the excess alkalinity and a bicarbonate buffered solution of sodium sulfide for the determination of the oxidizing capacity of the solution.

Although the previous examples have been inorganic reactions in water solution, the system described in the present invention is inclusive of any reacting fluids, suspensions, or combinations of phases before or after the reaction with inorganic or organic chemicals or combinations of both.

Table 1 demonstrates the wide variety of chemical concentrations which are determinable through the use of the present invention but is by no means a limitation of the invention.

TABLE 1

| Active Chemical in Sample Stream | | Reagent | |
|---|---|---|---|
| No. 1 | No. 2 | No. 1 | No. 2 |
| NaOH | | NaHCO$_3$ | |
| Na$_2$S | Na$_2$S$_2$O$_3$ | NaHCO$_3$ | H$_2$O$_2$ |
| NaOH | NaOCl | NaHCO$_3$ | Na$_2$S |
| NaOH | H$_2$O$_2$ | NaHCO$_3$ | Na$_2$S |
| H$_2$SO$_4$ | | NaOH | |
| HCl | | NaOH | |
| NaOH | | H$_2$SO$_4$ | |
| ClO$_2$(H$_2$O) | | Na$_2$S | |
| Cl$_2$(H$_2$O) | | Na$_2$S | |
| NH$_4$OH | | HCl | |
| NH$_3$(gas in air) | | Water | |
| NaOH (very strong) | | Water (dilution) | |
| H$_2$SO$_4$ (strong) | | Water (dilution) | |
| H$_2$SO$_3$ | | H$_2$O$_2$ | |
| Na$_2$SO$_3$ | | H$_2$O$_2$ | |

While embodiments of the invention have been described in detail, it will be obvious to those skilled in the art that the invention may be practiced otherwise than specifically described without departing from its scope as set forth in the following claims.

I claim:
1. A process for continuously determining the concentration of at least one chemical substance in a moving fluid sample stream which comprises:
mixing an excess of a reagent stream with said fluid sample stream to form a final reacted mixture stream, said reagent stream being reactive with said chemical substance to produce either an exothermic or endothermic reaction;
regulating the temperature of said reagent stream so that the temperature of the final reacted mixture stream approximates the temperature of the reagent stream, or regulating the temperature of the sample stream so that the temperature of the final reacted mixture stream approximates the temperature of the reagent stream; and then determining the concentration of the chemical substance in accordance with the following equation:

$$X = \frac{V_1(T_3-T_1) + V_2(T_3-T_2)}{C V_1}$$

where
 X is said concentration of at least one chemical substance, in said sample stream;
 $T_1$, $T_2$ and $T_3$ represent the temperatures of said sample stream, reagent stream and final reacted mixture stream, respectively;
 $V_1$ represents the flow rate of said sample stream;
 $V_2$ represents the flow rate of said reagent stream; and
 C is a factor which equals $$\frac{(\Delta H_{Reaction}) \text{ (heat capacity of the sample stream)}}{\text{molecular weight of the chemical substance being determined.}} \times \% \text{ completion}$$

2. A process, as in claim 1, wherein the temperature of the reagent stream is regulated by means of an external heating or cooling element to approximate the temperature of the reacted mixture stream.

3. A process, as in claim 1, wherein the temperature of the reagent stream is regulated toward the temperature of the reacted mixture stream by passing said reacted mixture stream in heat exchange with said reagent stream.

4. A process, as in claim 1, wherein the temperature of the sample stream is regulated so that the temperature of the final reacted mixture stream approximates the temperature of the reagent stream.

5. A process, as in claim 4, wherein the temperature of the sample stream is regulated by an external heating or cooling element.

6. A process as in claim 1, wherein both the sample stream temperature and the reagent stream temperature are regulated.

7. A process for continuously sequentially determining the concentration of more than one chemical substance in a moving fluid sample stream which comprises:
 mixing an excess of a reagent stream with said fluid sample stream to form a final reacted mixture stream, said reagent stream being reactive with said chemical substance to produce either an exothermic or endothermic reaction;
 regulating the temperature of said reagent stream so that the temperature of the final reacted mixture stream approximates the temperature of the reagent stream, or regulating the temperature of the sample stream so that the temperature of the final reacted mixture stream approximates the temperature of the reagent stream; and then
 determining the concentration of the chemical substance in accordance with the following equation:

$$X = \frac{V_1(T_3-T_1) + V_2(T_3-T_2)}{C V_1}$$

where
 X is said concentration of at least one chemical substance, in said sample stream;
 $T_1$, $T_2$ and $T_3$ represent the temperatures of said sample stream, reagent stream and final reacted mixture stream, respectively;
 $V_1$ represents the flow rate of said sample stream;
 $V_2$ represents the flow rate of said reagent stream; and
 C is a factor which equals $$\frac{(\Delta H_{Reaction}) \text{ (heat capacity of the sample stream)}}{\text{molecular weight of the chemical substance being determined;}} \times \% \text{ completion}$$

and then employing the resultant reacted mixture stream as a further fluid sample stream in an additional chemical substance concentration determination which comprises:
 mixing an excess of an additional reagent stream with said further fluid sample stream to form a final reacted mixture stream, said additional reagent stream being reactive with said chemical substance to produce either an exothermic or endothermic reaction;
 regulating the temperature of said additional reagent stream so that the temperature of the final reacted mixture stream approximates the temperature of the additional reagent stream, or regulating the temperature of the further sample stream so that the temperature of the final reacted mixture stream approximates the temperature of the additional reagent stream; and then
 determining the concentration of the chemical substance in accordance with the following equation:

$$X = \frac{V_1(T_3-T_1) + V_2(T_3-T_2)}{C V_1}$$

where
 X is said concentration of at least one chemical substance, in said further sample stream;
 $T_1$, $T_2$ and $T_3$ represent the temperatures of said further sample stream, additional reagent stream and final reacted mixture stream, respectively;
 $V_1$ represents the flow rate of said further sample stream;
 $V_2$ represents the flow rate of said additional reagent stream; and
 C is a factor which equals $$\frac{(\Delta H_{Reaction}) \text{ (heat capacity of the additional sample stream)}}{\text{molecular weight of the chemical substance being determined.}} \times \% \text{ completion}$$

* * * * *